(12) United States Patent
Safranski et al.

(10) Patent No.: US 10,390,980 B1
(45) Date of Patent: Aug. 27, 2019

(54) EXTRALUMINAL ENTEROGENESIS DEVICE

(71) Applicants: David L. Safranski, Atlanta, GA (US); Tom Jaksic, Boston, MA (US); Jeremy Gabriel Fisher, Atlanta, GA (US)

(72) Inventors: David L. Safranski, Atlanta, GA (US); Tom Jaksic, Boston, MA (US); Jeremy Gabriel Fisher, Atlanta, GA (US)

( * ) Notice: Subject to any disclaimer, the term of this patent is extended or adjusted under 35 U.S.C. 154(b) by 0 days.

(21) Appl. No.: 14/881,150

(22) Filed: Oct. 12, 2015

(51) Int. Cl.
*A61F 2/93* (2013.01)
*A61F 2/88* (2006.01)
*A61F 2/82* (2013.01)
*A61F 2/04* (2013.01)

(52) U.S. Cl.
CPC .......... *A61F 2/93* (2013.01); *A61F 2/88* (2013.01); *A61F 2/04* (2013.01); *A61F 2002/045* (2013.01); *A61F 2002/825* (2013.01); *A61F 2210/0014* (2013.01)

(58) Field of Classification Search
CPC ........ A61F 2/88; A61F 2/92; A61F 2002/045; A61F 2002/825; A61F 2/04; A61F 2/93; A61F 2210/0014
See application file for complete search history.

(56) References Cited

U.S. PATENT DOCUMENTS 8,709,034 B2 * 4/2014 Keast ............... A61B 17/221
606/185

* cited by examiner

*Primary Examiner* — Christopher D. Prone
(74) *Attorney, Agent, or Firm* — Morris, Manning & Martin, LLP; Bryan D. Stewart

(57) ABSTRACT

Provided herein are systems and methods for creating and deploying an entirely extraluminal enterogenesis device that is actuated during the enterogenesis period after the surgery is completed via an automatically controlled in-vivo activation of shape memory polymer network. This enterogenesis device operates to grow an extended body lumen without any significant interventions (e.g., via additional surgical intervention) over the period of lumen lengthening. Furthermore, the enterogenesis device operates outside the body lumen to lengthen the lumen without interfering with the lumen's internal activity during the period of the enterogenesis. The extraluminal enterogenesis device operates in an automatically-controlled manner over an extended period of time to provide the correct stimulus to grow the lumen into a lengthened state during the enterogenesis treatment period while providing high-quality continuous lumen activity during the treatment period without further intervention before distraction treatment is completed.

12 Claims, 10 Drawing Sheets

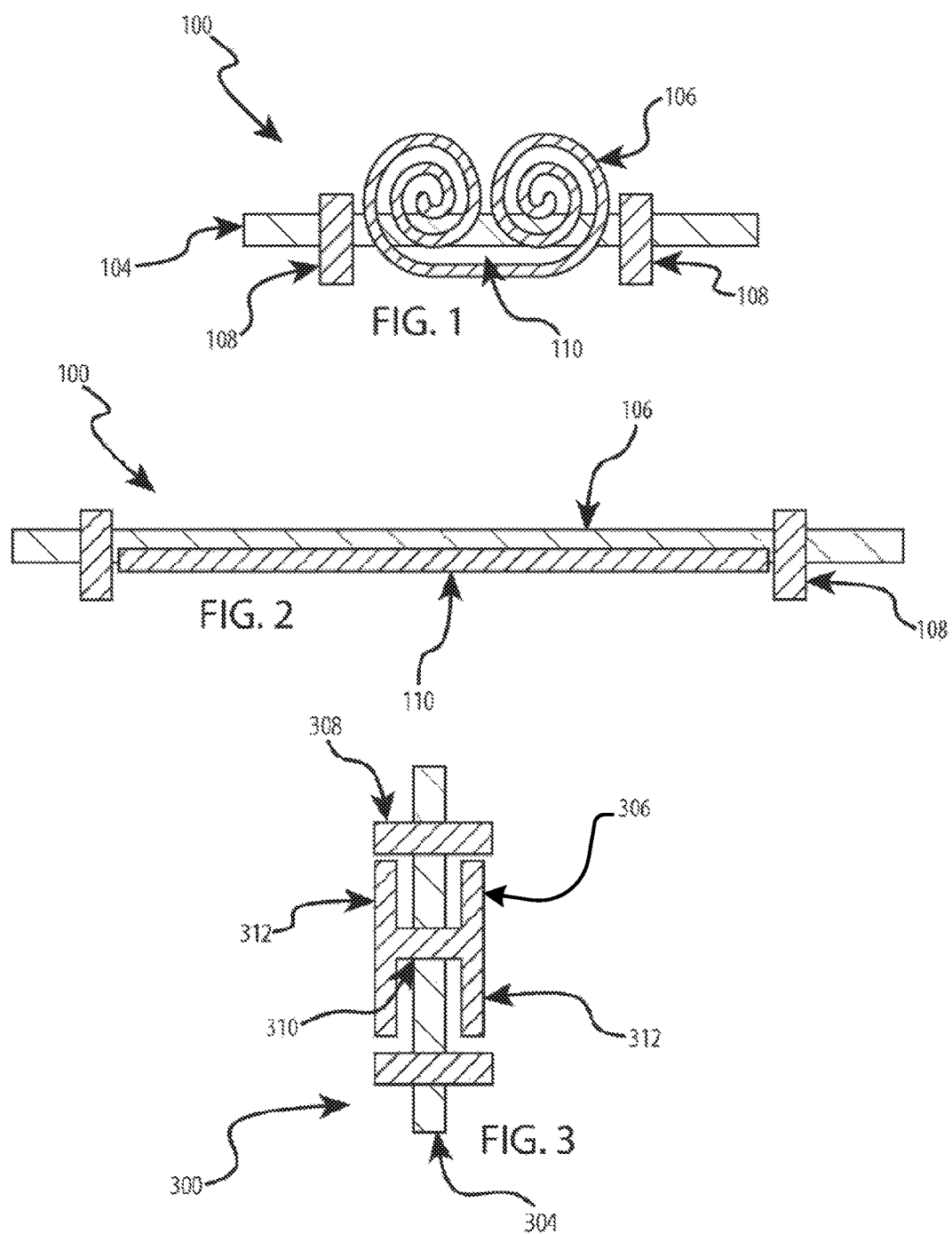

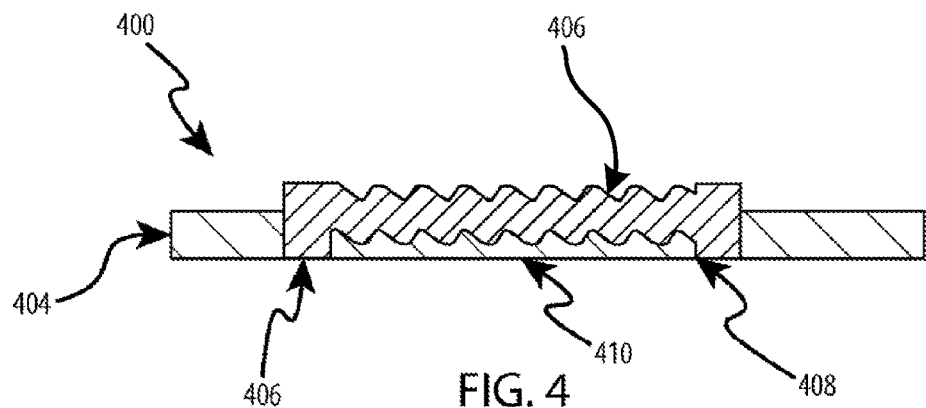
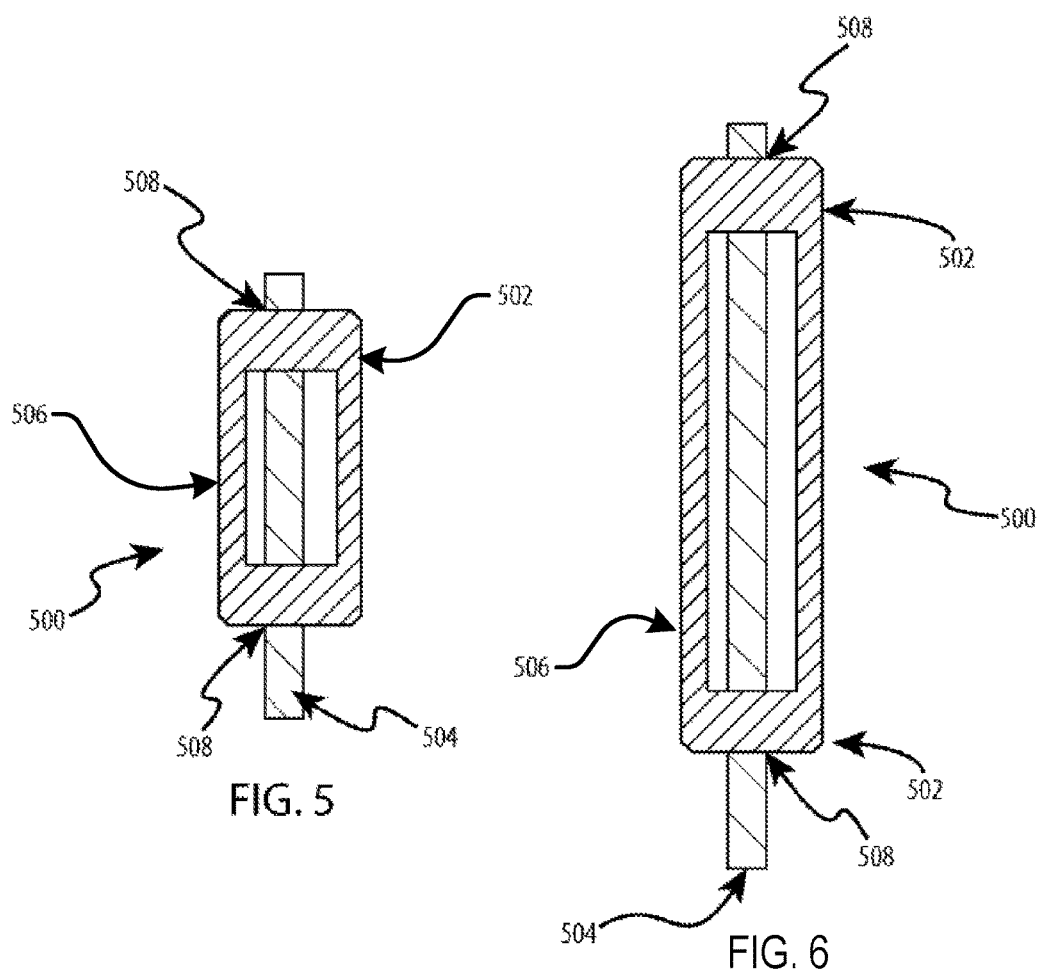

EXTRALUMINAL ENTEROGENESIS DEVICE

FIELD OF THE TECHNOLOGY

The present disclosure relates to enterogenesis methods, devices and systems operating to lengthen body lumens, particular enterogenesis devices that remain extraluminal.

SUMMARY OF THE DESCRIPTION

Provided herein are systems and methods for creating and deploying an entirely extraluminal enterogenesis device that is actuated during the enterogenesis period after the surgery is completed via an automatically controlled in-vivo activation of shape memory polymer network. This enterogenesis device operates to grow an extended body lumen without any significant interventions (e.g., via additional surgical intervention) over the period of lumen lengthening. Furthermore, the enterogenesis device operates outside the body lumen to lengthen the lumen without interfering with the lumen's internal activity during the period of the enterogenesis. Previous devices could interfere with the lumen's activity by opening the lumen during surgery to insert the device and by the device remaining inside the lumen during the period of enterogenesis. The extraluminal enterogenesis device operates in an automatically-controlled manner over an extended period of time to provide the correct stimulus to grow the lumen into a lengthened state during the enterogenesis treatment period while providing high-quality continuous lumen activity during the treatment period without further intervention before distraction treatment is completed.

In one aspect, the disclosure describes a medical device including an extraluminal mechanism configured to connect outside an intestinal lumen of a patient between two attachment points on the lumen. The extraluminal mechanism is further configured to create automatically a displacement distance between the two attachment points via actuation of the extraluminal mechanism before a first defined time elapses while the extraluminal mechanism is exposed to a first exposure environment of two different exposure environments. The extraluminal mechanism is further configured to create automatically the displacement distance between the two attachment points via actuation of the extraluminal mechanism only after a second defined time while the extraluminal mechanism is exposed to a second exposure environment of the two different exposure environments. The extraluminal displacement mechanism includes a self-activated shape memory polymer system with an inherent glass transition temperature of greater than 80 degrees Celsius. The self-activated shape memory polymer system is further configured to be activated solely via a first exposure to a 37 degrees Celsius physiological saline fluid and regulated for that first exposure to induce an early activation transition that occurs within the first defined time of no greater than 168 hours of exposure. The self-activated shape memory polymer system is further configured to be activated solely by second exposure to 37 degrees Celsius air at atmospheric pressure and relative humidity between 50 and 60 percent and regulated for that second exposure to induce a late activation transition that occurs only after the second defined time of greater than 500 hours of exposure.

Other embodiments and features of the present disclosure will be apparent from the accompanying drawings and from the detailed description which follows.

BRIEF DESCRIPTION OF THE DRAWINGS

The embodiments are illustrated by way of example and not limitation in the Figures of the accompanying drawings in which like references indicate similar elements.

FIG. 1 illustrates an embodiment of an enterogenesis device in a pre-actuated state, showing an embodiment with strain stored in a double-coil-shaped shape memory polymer element.

FIG. 2 illustrates an embodiment of an enterogenesis device in a fully-actuated state, showing an embodiment with a shape memory polymer element that has completely recovered an unconstrained shape.

FIG. 3 illustrates a side-view of an embodiment of an enterogenesis device, showing an exemplary cross-support on a shape memory polymer element as it wraps, at least partially, the body lumen.

FIG. 4 illustrates an embodiment of an enterogenesis device in a pre-actuated state, showing an embodiment with strain stored in a zig-zag shape memory polymer element.

FIG. 5 illustrates a side-view of an embodiment of an enterogenesis device, showing an exemplary cross-support on a shape memory polymer element at the ends while the shape memory polymer is in an undeployed state.

FIG. 6 illustrates a side-view of an embodiment of an enterogenesis device, showing an exemplary cross-support on a shape memory polymer element at the ends while the shape memory polymer element is in deployed state.

DESCRIPTION

Figure 7:
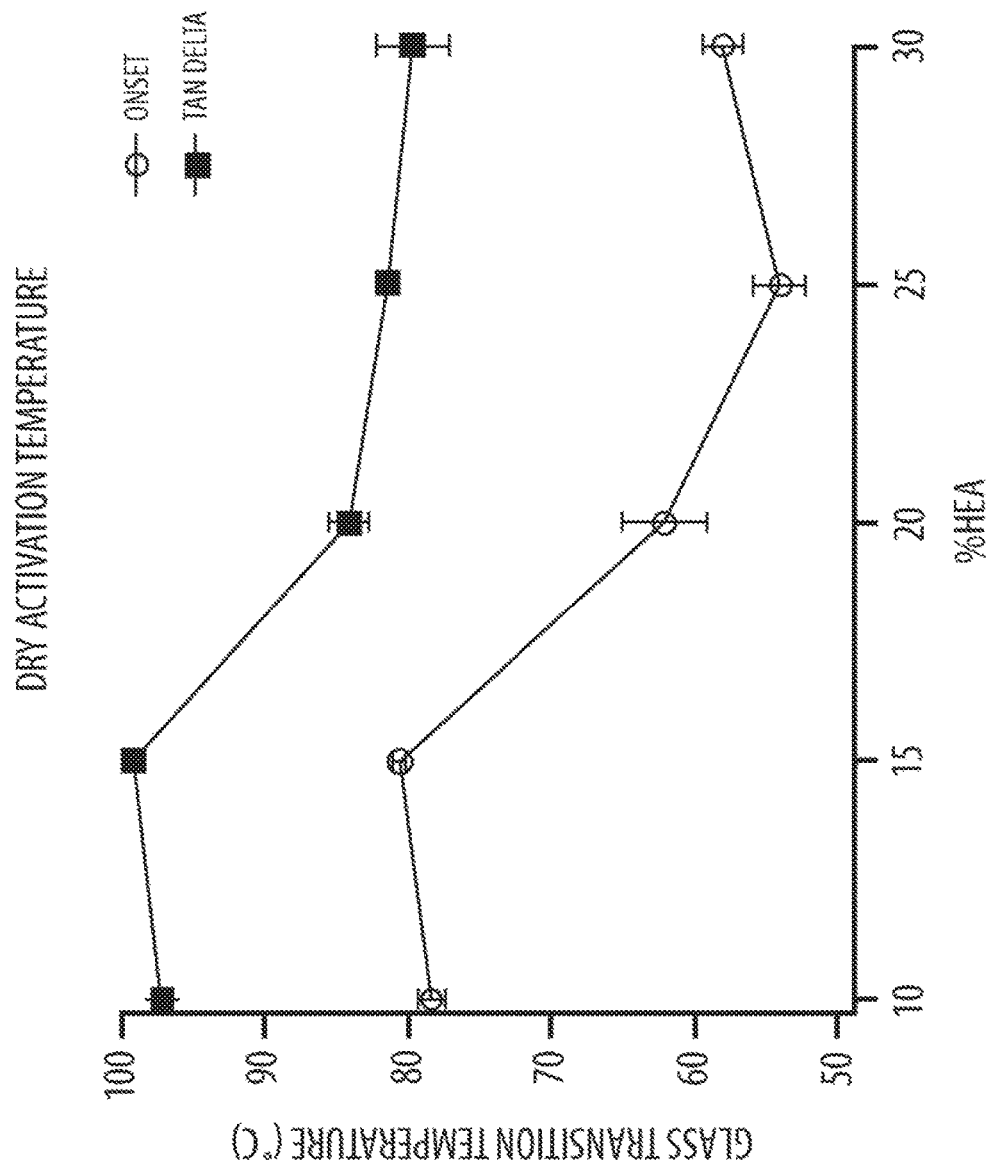
FIG. 7 illustrates exemplary data of activation temperatures in dry environments for different shape memory polymer networks with different percentages of HEA in networks tested for use as a shape memory polymer element with controlled automatic activation in enterogenesis devices herein.

The following patent description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment; and, such references mean at least one. Reference in this specification to "one embodiment" or "an embodiment" or the like means that a particular feature, structure, or characteristic described in connection with the embodiment is included in at least one embodiment of the disclosure. The appearances of the phrase "in one embodiment" or the like in various places in the specification are not necessarily all referring to the same embodiment, nor are separate or alternative embodiments mutually exclusive of other embodiments. Moreover, various features are described that may be exhibited by some embodiments and not by others.

FIG. 1 illustrates an embodiment of an enterogenesis device 100 in a pre-actuated state, showing an embodiment with strain stored in a double-coil-shaped shape memory polymer element 106. The enterogenesis device may be used to produce additional lumen 104 growth in patients.

Distraction enterogenesis is creating intestinal tissue by gentle sustained mechanical stretching over a period of time while new growth occurs. Distraction enterogenesis is therefore a promising new therapy for short bowel syndrome (SBS). The applied gentle and sustained tension applied by the distraction enterogenesis device induces growth of viable new lumen tissue. Enterogenesis produces this growth via several known molecular mechanotransduction pathways and stimulates mesenteric neovascularization. After enterogenesis, the test stretched jejunal segments appear to function well when replaced into continuity. Despite the number of devices now described in the literature, none has yet been translated into clinical practice or an approved working device. The extant approaches are relatively complex and have significant limitations, such as the need to violate the bowel wall, the use of a closed loop, or the need for a complex activating mechanism and multiple surgical iterations. The present disclosure describes a self-expanding polymer controlled extraluminal enterogenesis device that elongates small bowel and appears to induce growth without need for further surgical interventions before the removal of the device after enterogenesis treatment has completed.

Experimentally distraction on bowel has been shown to produce additional tissue (enterogenesis) and a variety of devices and operative approaches have been used in animals, but none of these strategies have yet translated into clinical use. Most of these devices must be placed within the lumen of the bowel, necessitating violation of the bowel wall, creation of a closed loop, and potentially damaging the mucosa. Some other devices require complex activation mechanisms that require external activation. Further, no other devices are FDA cleared or directly predicated on a cleared device.

Extraluminal configurations described herein include shape memory polymer elements between two attachment points of the extraluminal device for attaching the device between two portions of the lumen in order to provide a stretching force. As described herein, the stretching force is automatically controlled by a self-activation of a shape memory polymer that effectively expands a distance between and/or develops a stress between the two attachment points. As described further herein, the shape memory polymer activates to expand this distance or develop this stress against the lumen in a controlled manner over an extended period of time. Also as described further herein, the extended period of controlled activation of the shape memory polymer element may be further controlled by specific chemistry of the shape memory polymer network included in the element in addition to the shapes chosen for the element.

The embodiment of an enterogenesis device 100 shown has a double coiled shape memory polymer element 106 that provides distraction between two attachment points of the lumen 104, shown as collars 108 against which the shape memory polymer element presses. The embodiment shown generally shows the double coiled section 106 pressing laterally on the attachment points 108 in a constrained or stored strain shape and ready to be activated to cause the distraction. The attachment points 108 may be connected to a coil member of the double coil 106, or integrated with a portion of the coiled member, or free to move against the double coil member. The attachment points 108 themselves may be created to be a portion of the device, or separate collars, as diagramed with the coils 106 pressing against a separate collar 108. Attachment points or separate collars 108 may be attached directly to the lumen 104, such as via suturing.

The attachment points 108 may be supplemented in between by one or more additional attachment points 110, such as a point near the center of the shape memory polymer element 106. This attachment point 110 may be formed with a suture placed through the device 100 (e.g., at the shape memory polymer element 106) and into the lumen 104. An intermediate attachment point 110 between the collars 108 may be used to isolate one part of the activation of the shape memory polymer element 106 from affecting or being affected by the activation of another part of the element. For example, an attachment point 110 at the middle of the enterogenesis device 100 may be used to create two or more different activation results from two or more portions of the shape memory polymer element 106, leading to further ability to tailor the enterogenesis device for proper automatic and self-controlled deployment over a period of days or weeks.

The double coil is an exemplary stored strain for shape memory polymer elements used for the enterogenesis devices described herein. The stored strain can be seen completely recovered in FIG. 2, in this case, showing an unconstrained recovered shape that completely straightens the double coil shape and thus separates slowly the attachment points or collars and the attached body lumen points.

This uncoiling of the double coil element 106 is an exemplary shape change for the shape memory polymer element to store and unload strain and thereby effect the distraction enterogenesis treatment. Other stored strains are described herein and may be created to cause particularly controlled unloading of strains for beneficial enterogenesis results. As described further herein, the enterogenesis devices disclosed herein also use particular tailoring of the activation properties for the shape memory polymer element 106, and thus the deployment of the enterogenesis device 100 to distend the lumen 104, in an automatically controlled manner over an extended period of time.

FIG. 2 illustrates an embodiment of an enterogenesis device 100 in a fully-actuated state, showing an embodiment with a shape memory polymer element 106 that has completely recovered an unconstrained shape.

The enterogenesis device 100 is shown in FIG. 2 with the shape memory polymer element 106 exhibiting a complete strain recovery into a permanently stored and fully straightened shape. In one embodiment, a residual stress of the body lumen 104 could produce a residual stress on the element 106 even after the shape memory polymer has fully activated. For example, the straight shape of the element 106 shown may have a residual strain from a permanent non-straight shape.

A shape memory polymer network in the shape memory polymer element 106 of the enterogenesis device 100 does not need to fully recover its shape to its permanent shape even after being fully activated. Rather, an activated shape memory polymer may exhibit its activation in part or entirely as a generation of force against a constraint, such as the collars 108 or attachment points 110 of the enterogenesis device 100. Thus, the terms "activated" or "activation" as used herein describes a shape memory polymer exhibiting some combination of (1) stored strain shape recovery and (2) force production against a constraint restraining the recovery of that stored strain.

In many embodiments the unconstrained and fully activated shape (e.g., the permanent shape) of the shape memory polymer device is not straight as it is shown here for simple illustration of completed recovery. The unconstrained fully activated shape may include complex bends, shapes and other structures even after the permanent shape is restored with no further enforced or stored strain. For example, the unconstrained fully activated shape as well as intermediate shapes during recovery may be configured to provide the correct distance and mechanical support between attachment points 108 of the enterogenesis device 100. Each of these requirements should also allow the device to operate outside the lumen 104 and not unduly interfere with the operation of the lumen during the treatment period.

FIG. 3 illustrates a side-view of an embodiment of an enterogenesis device 300, showing an exemplary cross-support 310 on a shape memory polymer element 306 as it wraps, at least partially, the body lumen 304.

The shape memory polymer element 306 may be shaped to support the enterogenesis lumen lengthening process between the two attachment points via preventing torsion, curling, or other out of axis or out of plane movement that is not desired during the extended period of activation. For example, cross-supports 310 and other types of reinforcements may be used to span two or more side portions 312 of the shape memory polymer element 306 and create lateral and torsional stiffness in the shape memory polymer element. The cross-supports 310 and other reinforcements can be made out of the same shape memory polymer or a different material. The cross-supports 310 may be made from a non-active or a non-shape memory material. In addition, the cross-supports 310 may be made of active materials and include non-active portions and portions with different strain directions and magnitudes than the side portions 312 of the shape memory element 306.

FIG. 4 illustrates an embodiment of an enterogenesis device 400 in a pre-actuated state, showing an embodiment with strain stored in a zig-zag shape memory polymer element 406.

Several shapes can be used to store compressive, expansive, twisting or other strains, via various mechanical interfaces, to create distraction of the lumen 404 between two attachment points 408. As described above, the enterogenesis device 400 may be attached to the lumen 404 at a mid-point 410 between the attachment points 408 and thereby create two portions of lumen 404 that may be controllably under tension from two portions of the shape memory polymer element 406 on either side of the mid-point attachment point. Complex shapes of the shape memory polymer element 406 may be used to create the distracting forces between any of the attachment points 408 or 410.

Stored strains and recoveries may also be programmed in complex ways as illustrated by the zig-zag shape of the shape memory polymer element 408, with the straight or straighter shape being recovered over an extended period of time as distracting forces are applied between the attachment points 408. The strains stored by a shape memory polymer element 406 in a zig-zag shape are complex strains, with multiple transitions between types of strains, bending, compressive and stretching. These strains cannot exceed limits of strain before failure, so there are practical limits to the shapes and complexities of the stored strains that are used for the shape memory polymer element 406 in the enterogenesis device 400.

FIG. 5 illustrates a side-view of an embodiment of an enterogenesis device 500, showing an exemplary cross-support on a shape memory polymer element at the ends 502 while the shape memory polymer element 506 is in an undeployed state.

The embodiment of the shape memory polymer element 506 in a zig-zag shape may include a similar side view, such as if the side view shown has complex bends directly perpendicular to the page and not seen in profile or side-view. In other embodiments, zig-zagging bends may be used in multiple dimensions, such as in a cage-like structure.

The embodiment shown has attachment points 508 for attaching to the lumen 504 at the ends 502 of the enterogenesis device 500. These attachment points 508 may be active or inactive in creating further distraction forces or movement through shape memory polymer activation of the shape memory polymer element 506. The shape memory polymer element 506 may be integrated into the portions of the ends and/or collars and/or attachment points of the enterogenesis device 500. As described further herein, the ends 502 and attachment points 508 may be connected by a combination of materials, with both active and/or inactive properties.

FIG. 6 illustrates a side-view of an embodiment of an enterogenesis device 500, showing an exemplary cross-support on a shape memory polymer element 506 at the ends while the shape memory polymer element is in a deployed state.

There are many deployed states possible for the shape memory polymer element 506 that include an equilibrium between stress and strain residing in the shape memory polymer element upon full activation of the shape memory polymer. As described further herein, the possible complexity in shape and strains of the shape memory polymer element are limited 506 practically by strain to failure limits of the shape memory polymer network used to store the strain. Cross-supports and other complex shapes are not shown as they are described further herein and a simply cylindrical side-view may be used here to represent simply the deployed state of the enterogenesis device 500. However, other embodiments are possible with cross-supports or zig-zags in multiple directions and/or surrounding the lumen 504 for example, surrounding the lumen as a cage, web, or mesh. Further, the open construction shown in the open cross-section serves to emphasize that the shape memory polymer element 506 remains extraluminal throughout the enterogenesis treatment process.

The term "extraluminal" as used herein excludes incidental violations of the wall of the lumen 504 for attachment, such as for suturing to the lumen an attachment point 508. Thus, sutures and other attachment devices, even if they are integrated or attached to the enterogenesis device 500, are still considered completely extraluminal for this disclosure.

FIG. 7 illustrates exemplary data of activation temperatures in dry environments for different shape memory polymer networks with different percentages of HEA in networks tested for use as a shape memory polymer element with controlled automatic activation in enterogenesis devices herein. Dry environment activation data is discussed here for standardization purposes even though during operation of the device for all intended uses, the device and shape memory polymer will be exposed to the internal fluids. The "dry activation" response helps characterize a difference of a "wet activation" in the presence of physiological fluids (further standardized for testing as physiological saline). Manipulations in the shape memory polymer networks are shown further herein via their activation characteristics in both wet and dry environments. These manipulations allow for the enterogenesis devices herein to exhibit automated activation that is self-controlled to extend activation forces and shape change to create an extended activation over a period of one week to several weeks during the enterogenesis treatment period.

As an exemplary embodiment of a shape memory polymer used in the experiments herein, to create the polymer, isobornyl acrylate, 2-hydroxyethylacrylate (HEA), and 1,6-hexanediol diacrylate (HDDA) were mixed in weight ratio of 75:20:5, respectively. Other acrylate based networks may be used to create shape memory polymer networks with similar characteristics, based on the properties and characteristics of those networks as described and claimed herein. In the exemplary networks described herein, 0.5 wt % of phenylbis(2,4,6-trimethylbenzoyl)phosphine oxide was used as a photoinitiator. All reagents were used as received (Sigma-Aldrich, St. Louis, Mo.).

The networks shown were made with various percentages of 10%-30% HEA. When tested for their glass transition temperatures, the data shows that each network has a significantly higher glass transition temperature (when measured both at onset and at peak tan delta of the transition) than physiological temperatures. Indeed, many of the data points, both for onset and peak tan delta are at temperatures that will kill living tissue in a patient. However, uptake of solvent (e.g., water) by the shape memory polymer effectively lowers glass transition temperature of the network. Characterizations of the various polymer networks tested in designing a functional therapeutic distraction enterogenesis device identify suitable networks with large differences in their wet activations and dry activations and appropriately extend the controlled wet activations to occur within days, many times faster than dry activations of the same networks.

The shape memory polymer networks described herein are designed to dramatically modify their activation response based on the presence of a solvent (e.g., water) in the activation environment. The dry activation process is intentionally designed to be slow and resist activating beyond several weeks. For example, suitable characterizations of dry activations may require one to five weeks or more of activation time to reach an activation threshold (i.e., 50% unconstrained shape recovery). Time thresholds for the activation transition during dry activation can be set for long time periods ranging from 168 hours (7 days), 336 hours (14 days), 504 hours (21 days), four weeks, and through extreme times to complete activation, where no noticeable response occurs for long periods of time.

Conversely, the wet activation process designed to be relatively fast (e.g., within two days, within a week). Specifically, while a dry environment at a physiological temperature of 37 degrees Celsius produces little or no activation while a wet environment, with the simple introduction of saline to distinguish activation before and after surgical implantation, a wet activation produces a dramatic increase in activation rate, allowing complete activation within a shortened activation threshold of as little as one to several days. For example, thresholds for characterizing wet activations may include short times for activation thresholds for enterogenesis of soft tissues like 24 hours (e.g., which may be suitable for softer networks). As other examples, thresholds for characterizations of activation thresholds in test wet environments such as physiological saline can be anywhere from several hours to several days, or a week, namely 168 hours. These wet activation thresholds can be tailored with particular chemistries and/or methods of imparting and storing the strain in the shape memory polymer networks.

Thus, the use of the testing environments for wet and dry activation that approximating physiological characteristics should be understood as descriptive and illustrative of the different activations achievable by the shape memory polymer networks described herein, and not confused with how the networks will be used in enterogenesis devices during treatment in actual physiological environments. Other properties of the shape memory polymer networks are also described herein for illustration and characterization of the shape memory polymer networks. These descriptions are meant to describe the without necessarily describing those properties or activations as being used during surgery or in an implanted enterogenesis device.

Figure 8:
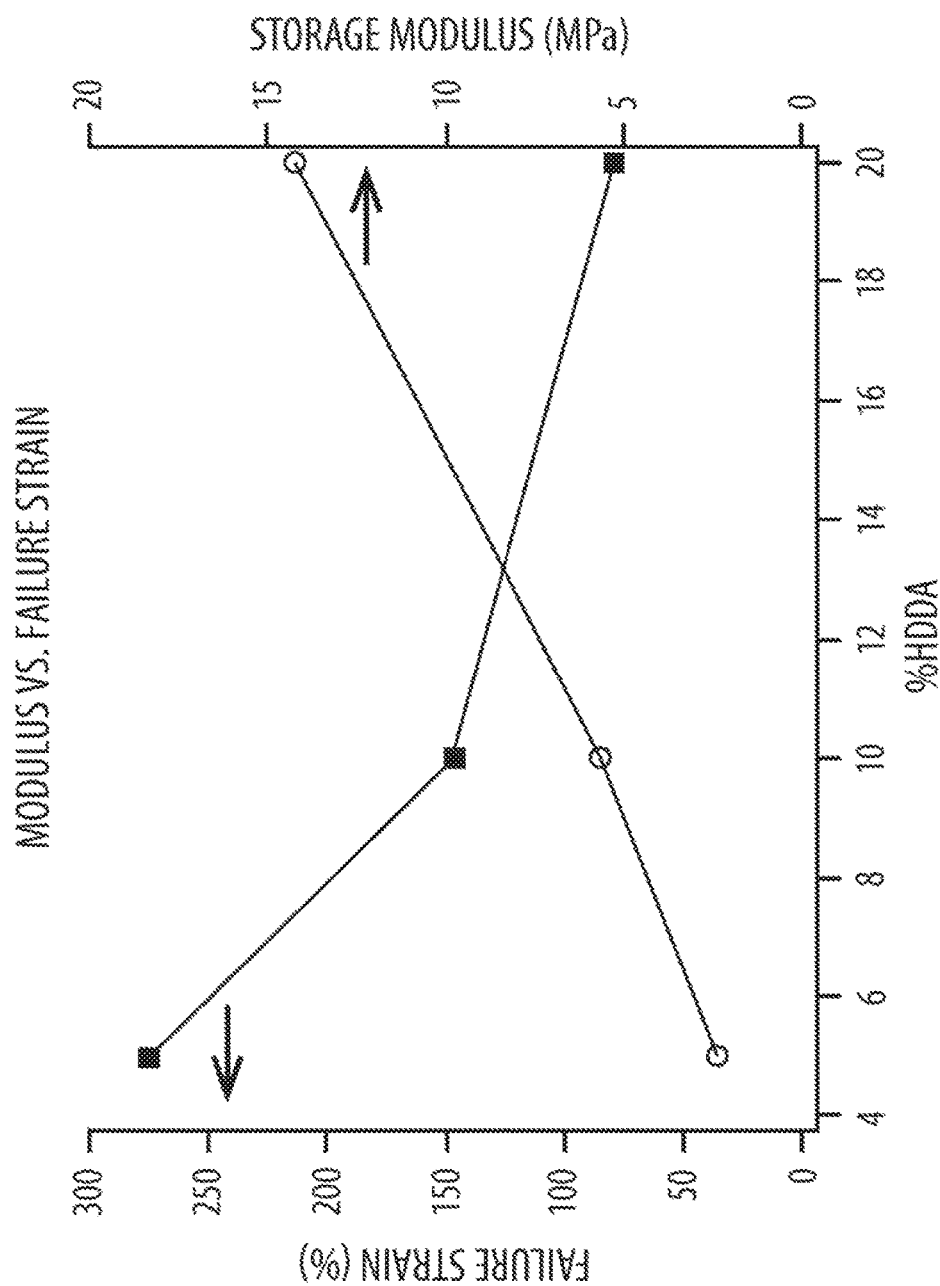
FIG. 8 illustrates exemplary data of storage modulus and failure strain for different shape memory polymer networks with different percentages of HDDA for shape memory polymer networks tested for use as a shape memory polymer element with controlled automatic activation in enterogenesis devices herein.

FIG. 8 illustrates exemplary data of storage modulus and failure strain for different shape memory polymer networks with different percentages of HDDA for shape memory polymer networks tested for use as a shape memory polymer element with controlled automatic activation in enterogenesis devices herein.

HDDA has an effect of controlling both the stiffness of a shape memory polymer network, and the maximum strain before failure attainable by that network. The storage modulus raises with increased HDDA percentage in the networks, while the potential failure to strain decreases for those networks. The ranges of percentages used for test shape memory polymer networks used herein are shown in the graph from 5-20% HDDA. However, 20% samples had a low enough maximum strain to failure value that prototypes were unable to store enough strain to bend into many tested temporary shapes.

As shown in the embodiments shape memory polymer elements herein, the strain stored in the shape memory polymer networks must be stored below this failure strain value if strained failures are not going to compromise the SMP element during and after recovery. Strains may be concentrated in certain regions (such as sharp bends, along or across surfaces, etc.) based on the shape of the element that stores the strain. Any stored strain that is greater than the strain to failure of the network can create failures that weaken the element, even if those failures only are localized where the strain was greatest.

Figure 9:
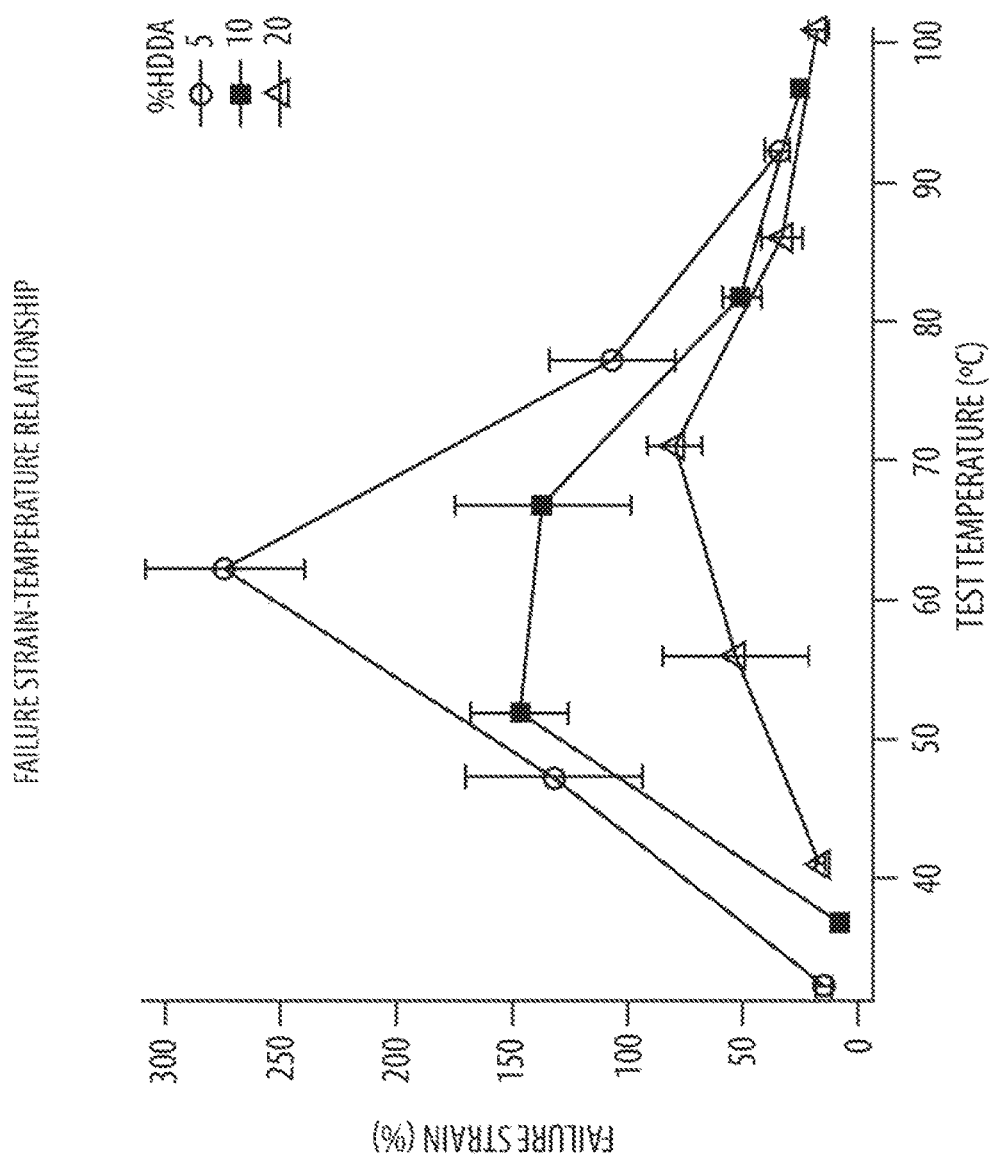
FIG. 9 illustrates exemplary data of failure strain versus temperature for different shape memory polymer networks with different percentages of HDDA for shape memory polymer networks tested for use as a shape memory polymer element with controlled automatic activation in enterogenesis devices herein.

FIG. 9 illustrates exemplary data of failure strain versus temperature for different shape memory polymer networks with different percentages of HDDA for shape memory polymer networks tested for use as a shape memory polymer element with controlled automatic activation in enterogenesis devices herein. As described above, maximum strain to failure became an issue for some samples of the shape memory polymer networks with 20% HDDA. This data was taken from shape memory polymer networks strained to failure at different temperatures, including networks with respectively 5% 10% and 20% HDDA. The HDDA strain to failure data shown herein differentiates the temperatures for which the maximum strain to failure values were collected for FIG. 8.

The variation in strains to failure due to temperature create additional selection possibilities for polymers making up a shape memory polymer element for an enterogenesis device. For example, a stored complex strain with different localized strain levels throughout a shape memory polymer element may have a portion or portions of strain that are above the maximum strain to failure the temperature of straining, such as setting the stored strain or imparting the shape memory polymer's temporary shape. Therefore, the shape memory polymer networks described herein are selected to allow the stored strain to be safely imparted at the correct temperature. As shown on the graph, the area under the curve approximates selection choice in both temperature of straining and in amount of strain possible before failure of that polymer network. Thus more complex and concentrated strains in shape memory polymer elements may be developed for networks with more area displayed under the curves shown.

Figure 10:
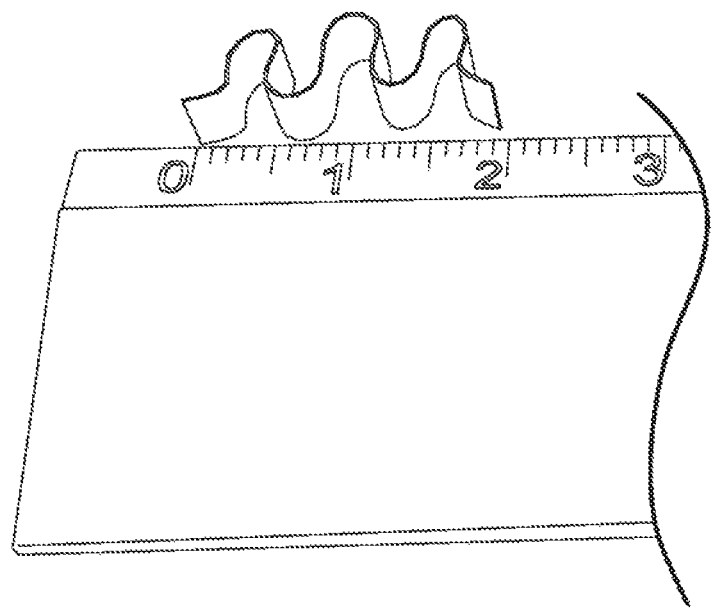
FIG. 10 shows an exemplary shape memory polymer element storing strain in a zig-zag type shape and measuring about 2 centimeters.

FIG. 10 shows an exemplary shape memory polymer element storing strain in a zig-zag type shape and measuring about 2 centimeters. The shape memory polymer element is shown next to a ruler showing the element measures from end to end about 2 centimeters in its zig-zag shape.

The embodiment of the zig-zag shape of the shape memory polymer element is shown as a smooth wave, in a shape similar to an oxbow river, or ribbon candy. This shape provides several benefits allowing for a compressed "back and forth" configuration that also avoids sharp bends that would concentrate strain and possibly lead to a failure where strain is over the strain to failure value for temperature at which the strain is set.

The unconstrained and fully recovered shape of the shape memory polymer element shown is a straight length of SMP measuring about 4.5 centimeters. Therefore, the overall strain as measured purely in the length of the device as shown against the ruler is a single compressive strain. However, the zig zag (e.g., curved ribbon) shape contains many different strains, including compressive, stretching, and possibly twisting or torsional strains. These strains vary drastically in magnitude and direction and provide a simple example of how complex strains can arise in even relatively complex storage configurations of the shape memory polymer element.

Figure 11:
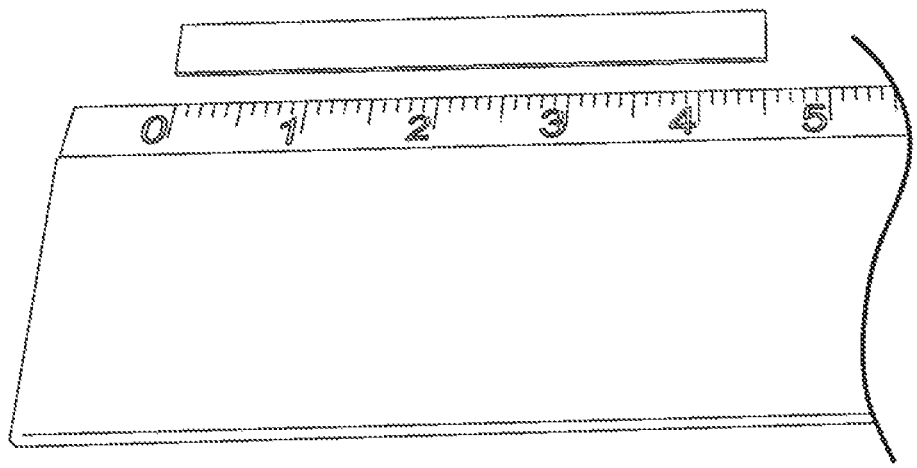
FIG. 11 shows the exemplary shape memory polymer element in an unconstrained straight shape and measuring about 4.5 centimeters.

FIG. 11 shows the exemplary shape memory polymer element in an unconstrained straight shape and measuring about 4.5 centimeters. The unconstrained shape is a straight bar and thus when the activation process is completed in an unconstrained environment, the element returns almost completely to this shape. The time required for completing the recovery in FIG. 11 was not measured for these trials as they were meant to demonstrate the completed states of full strain storage and full strain recovery for the shape memory polymer element.

Below normalized recovery values are shown and described with respect to timing for both dry environments and saline solution environments. The shape memory networks used herein are specially designed to have a distinct difference in activation response between the responses to these two environments at the same physiological temperature (e.g., 37 degree Celsius) as demonstrated by the side-by-side comparison of the data.

Figure 12A:
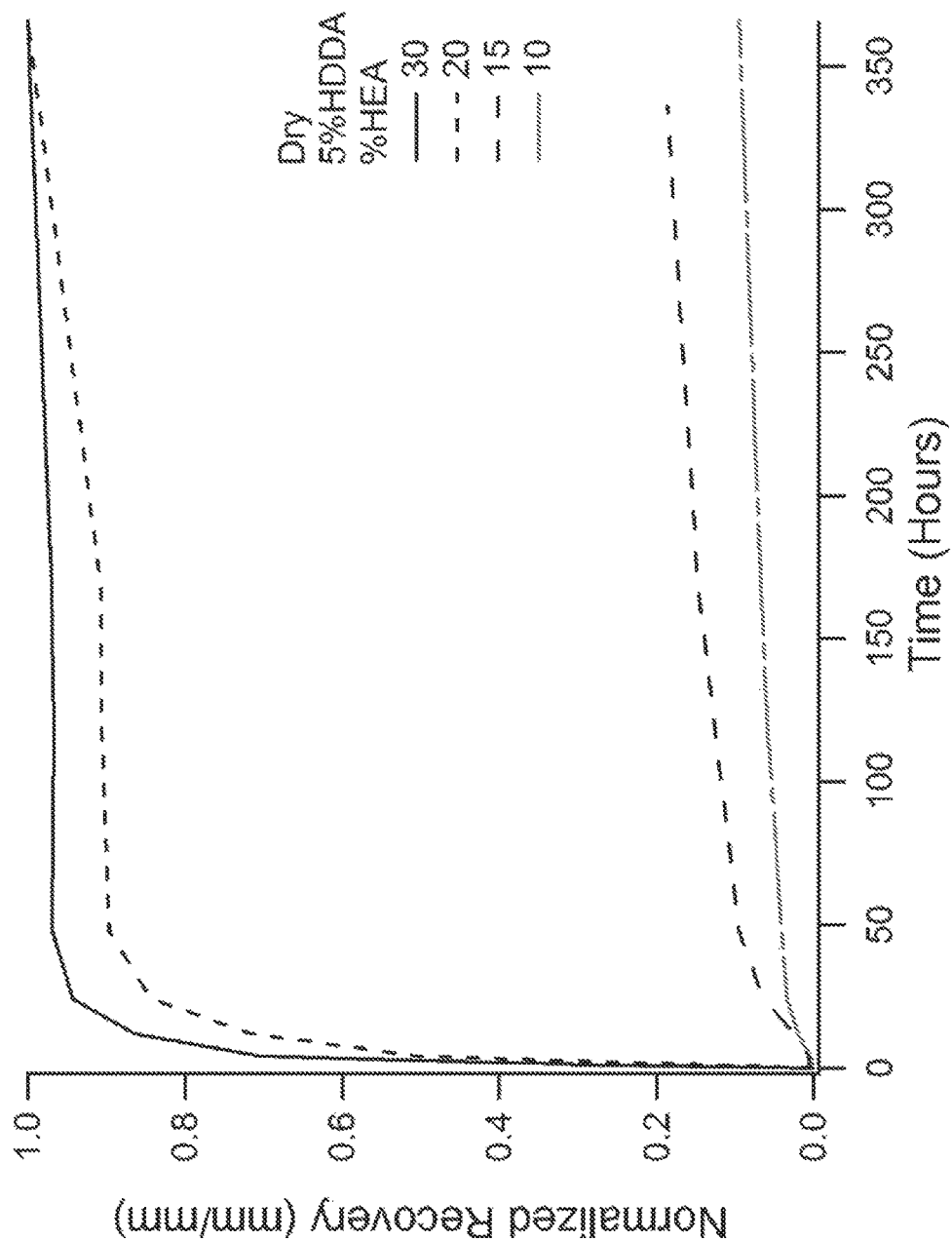
FIG. 12A illustrates exemplary data of normalized recovery versus time for shape memory polymer networks in a dry environment at 37 degrees Celsius for different shape memory polymer networks with different percentages of HEA in networks including 5 percent HDDA.

FIG. 12A illustrates exemplary data of normalized recovery versus time for shape memory polymer networks in a dry environment at 37 degrees Celsius for different shape memory polymer networks with different percentages of HEA in networks including 5 percent HDDA.

Figure 12B:
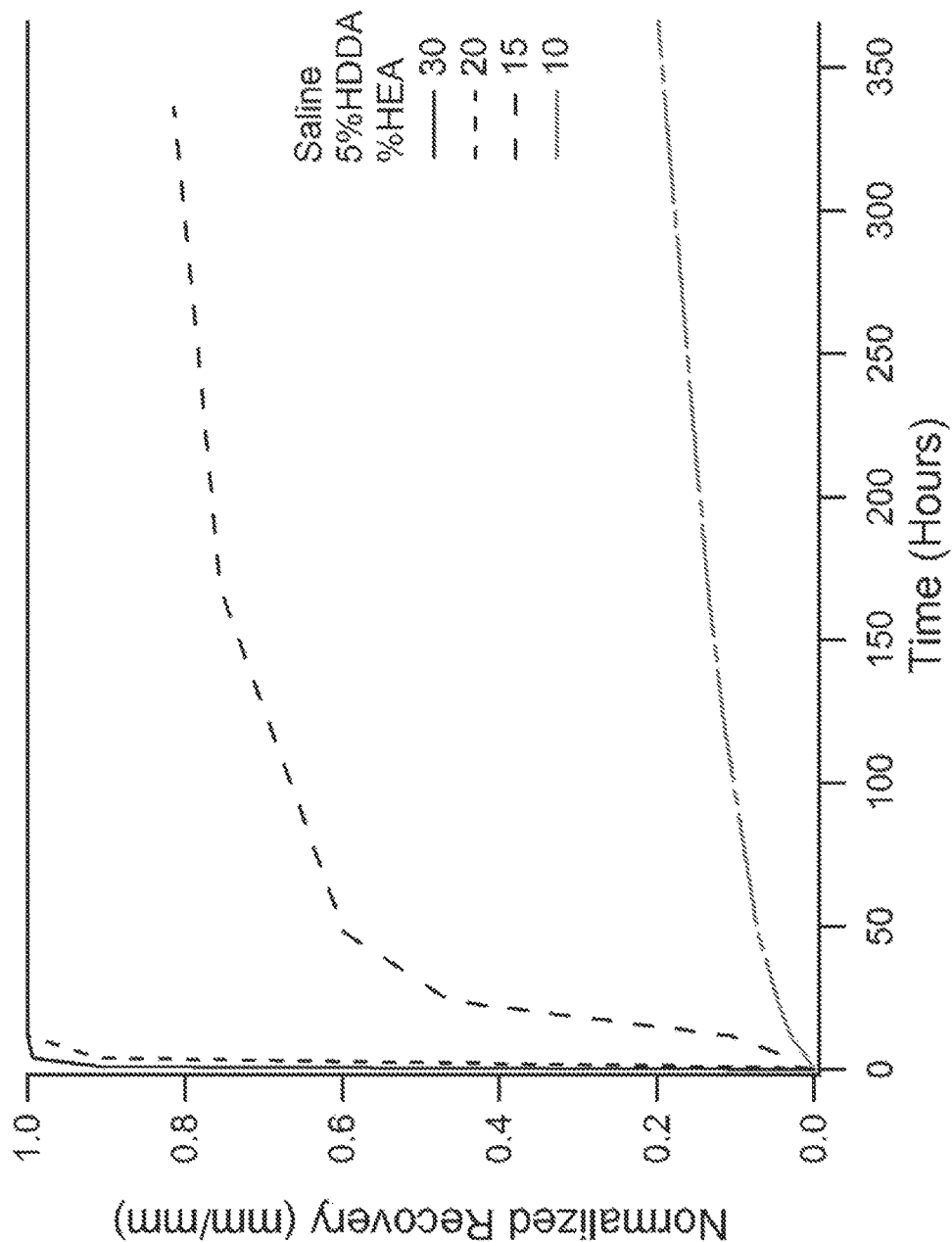
FIG. 12B illustrates exemplary data of normalized recovery versus time for shape memory polymer networks in a physiological saline environment at 37 degrees Celsius for different shape memory polymer networks with different percentages of HEA in networks including 5 percent HDDA.

FIG. 12B illustrates exemplary data of normalized recovery versus time for shape memory polymer networks in a physiological saline environment at 37 degrees Celsius for different shape memory polymer networks with different percentages of HEA in networks including 5 percent HDDA.

The data acquired from the various shape memory polymer networks are shown in FIG. 12A for trials in the dry environment and in FIG. 12B for trials in the saline environment. For both sets of trials, networks were created including 5 percent HDDA and alternately 30 percent, 20 percent, 15 percent and 10 percent HEA. For testing, samples of the networks were strained similarly before being tested for different recovery characteristics at 37 degrees Celsius. The times shown in the graph represent significantly extended recovery periods created by the significantly reduced recovery rates at the physiological temperature (e.g., 37 degrees Celsius) that is far below the tested dry glass transition temperature. Therefore, the recovery rates, without being accelerated via immersion in saline, cause a recovery transition (normalized shape recovery past 50%) only after an excess of 2 weeks for some networks but other networks have a recovery transition within hours, such as networks with 30 percent or 20 percent HEA. Because recovery measurements may be blurred by the long times, even in the standardized testing of dry environments and saline environments, as used herein the "recovery transition" for an unconstrained element means achieving normalized shape recovery of the stored strain of the element equal to 50%.

The normalized recovery (mm/mm) of each similarly strained sample is plotted versus time of exposure to the different environments. These differences in the data show a significant increase in activation rates between dry environment recovery and saline environment recovery for some networks, but not for others. For example, the network samples with 5 percent HDDA and 15 percent HEA recovered much differently in dry environmental conditions than they recovered in saline environments. Specifically, in dry conditions, the 15 percent HEA network recovers comparatively to the saline recovery of the 10 percent HEA network, whereas the same 15 percent HEA network recovers much more quickly in saline, more similarly to the dry recovery of both 20 percent HEA and 30 percent HEA networks. This significant increase in activation rates for the 5% HDDA and the 15% HEA networks indicate a candidate shape memory polymer network for use in the enterogenesis devices herein.

As described further herein, the increases in HDDA percentage had the effect of stiffening the network (increasing storage modulus) and decreasing the maximum strain that can be stored. Also, increasing the HEA percentage increases solvent (e.g., water) uptake into the network, accelerating the relaxation of the energy barriers to activation and effectively lowering the glass transition temperature of the network after the solvent is taken up. Designing and selecting a network as described herein with large differences between wet and dry activations and with significantly extended self-controlled activation to produce distinct activation responses allows the network to be integrated into an enterogenesis device with great therapeutic results.

Each of the recovery times are accelerated to complete a recovery transition earlier while being immersed in saline. However, networks that have significant differences between times before recovery transition in dry and saline environments are particularly designed and used for the enterogenesis devices as described herein due to their stability during shipment and handling and their proper self-controlled activation once inside the body.

Figure 13A:
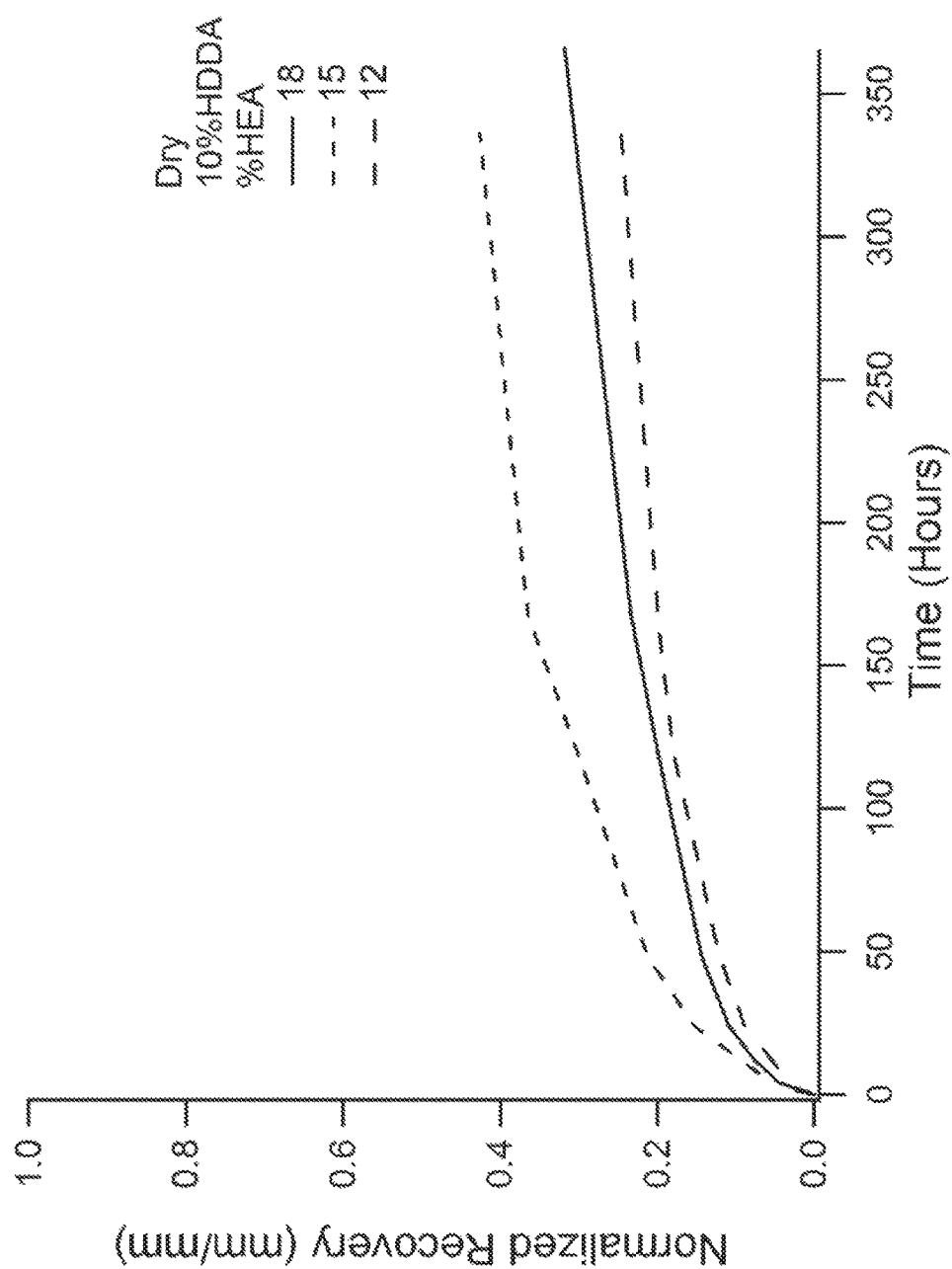
FIG. 13A illustrates exemplary data of normalized recovery versus time for shape memory polymer networks in a dry environment at 37 degrees Celsius for different shape memory polymer networks with different percentages of HEA in networks including 10 percent HDDA.

FIG. 13A illustrates exemplary data of normalized recovery versus time for shape memory polymer networks in a dry environment at 37 degrees Celsius for different shape memory polymer networks with different percentages of HEA in networks including 10 percent HDDA.

Figure 13B:
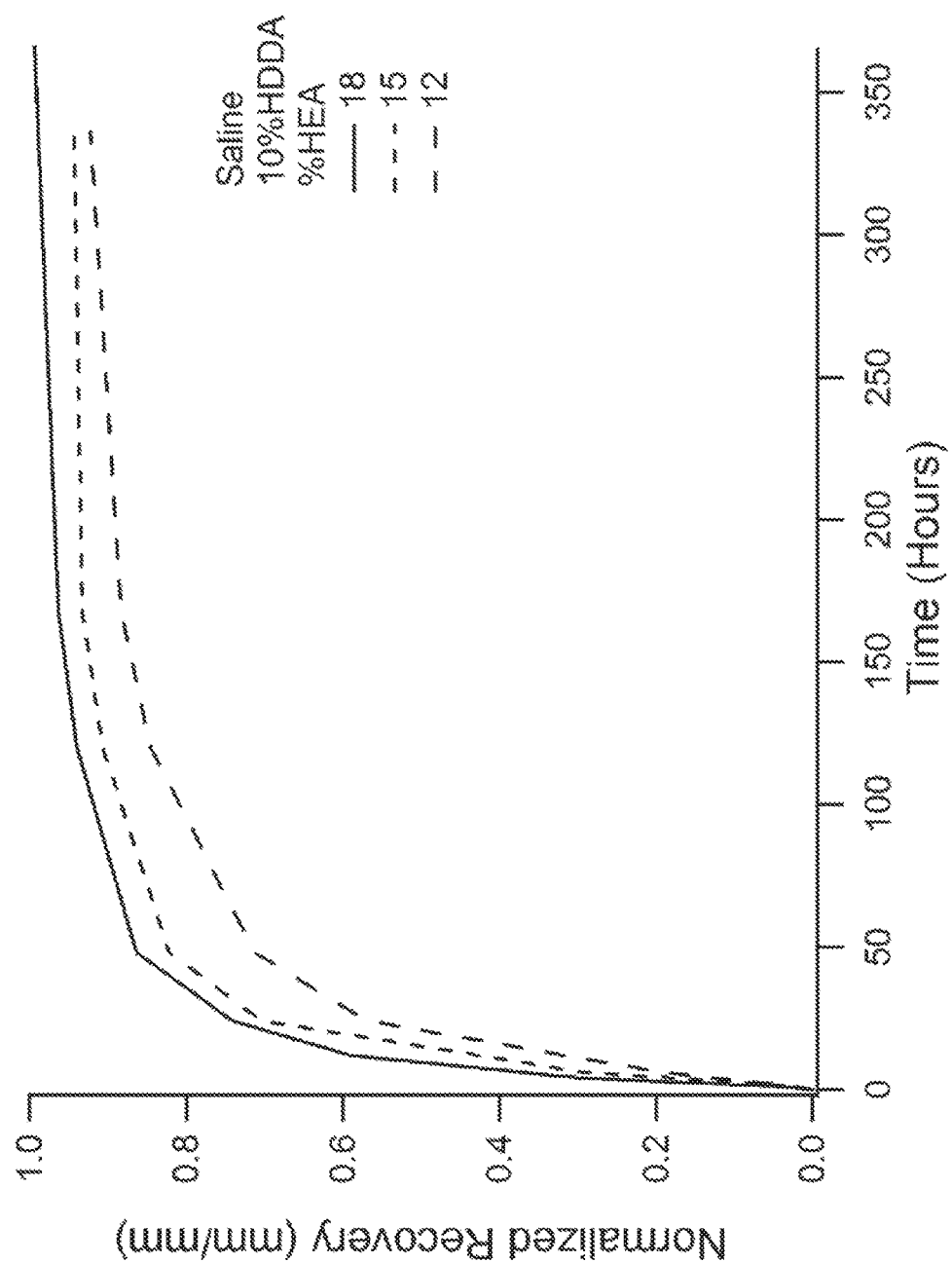
FIG. 13B illustrates exemplary data of normalized recovery versus time for shape memory polymer networks in a physiological saline environment at 37 degrees Celsius for different shape memory polymer networks with different percentages of HEA in networks including 10 percent HDDA.

FIG. 13B illustrates exemplary data of normalized recovery versus time for shape memory polymer networks in a physiological saline environment at 37 degrees Celsius for different shape memory polymer networks with different percentages of HEA in networks including 10 percent HDDA.

The networks and environments used for this data are similar to those used for FIG. 12, except shape memory polymer networks used for FIG. 13 comprise polymer compositions with 10 percent HDDA and alternatively 12 percent, 15 percent, and 18 percent HEA. Since each of the networks shown in this FIG. 13 have been preselected to be closely related to each other, their behavior is more closely matched than FIG. 12.

Each of the networks shows significant difference between the recoveries in dry environments and in saline environments. These networks thus can produce significant recoveries under surgical conditions whereas their dry counterparts will not significantly recover before exposure to the liquid environment of a patient's internal fluids approximated in tests herein via the physiological saline fluid.

This patent description and drawings are illustrative and are not to be construed as limiting. It is clear that many modifications and variations of this embodiment can be made by one skilled in the art without departing from the spirit of the novel art of this disclosure. While specific parameters, including device configurations, parameters of components, and thresholds may have been disclosed, other reference points can also be used. These modifications and variations do not depart from the broader spirit and scope of the present disclosure, and the examples cited here are illustrative rather than limiting.

What is claimed is:

1. A medical device, comprising:
an extraluminal displacement mechanism comprising:
a first length as measured along a longitudinal axis between two attachment points prior to activation of the extraluminal displacement mechanism;
a self-activated shape memory polymer system comprising isobornyl acrylate, HEA, and HDDA, wherein:
the extraluminal displacement mechanism is configured to:
connect outside an intestinal lumen of a patient between the two attachment points on the lumen;
create automatically a displacement distance between the two attachment points via actuation of the extraluminal displacement mechanism before a first defined time elapses while the extraluminal displacement mechanism is exposed to a first exposure environment of two different exposure environments;
create automatically the displacement distance between the two attachment points via actuation of the extraluminal displacement mechanism only after a second defined time while the extraluminal displacement mechanism is exposed to a second exposure environment of the two different exposure environments;
the extraluminal displacement mechanism has a second length as measured along the longitudinal axis after activation of the extraluminal displacement mechanism;
the second length is greater than the first length;
the extraluminal displacement mechanism exerts force on at least one of the two attachment points as it expands from the first length to the second length;
the self-activated shape memory polymer system is further configured to be activated solely via a first exposure to a 37 degrees Celsius physiological saline fluid and regulated for that first exposure to induce an early activation transition that occurs within the first defined time of no greater than 168 hours of exposure; and
the self-activated shape memory polymer system is further configured to be activated solely by second exposure to 37 degrees Celsius air at atmospheric pressure and relative humidity between 50 and 60 percent and regulated for that second exposure to induce a late activation transition that occurs only after the second defined time of greater than 500 hours of exposure.

2. The medical device of claim 1, wherein the activation transition is defined as achieving 50% shape recovery.

3. The medical device of claim 1, wherein the extraluminal displacement mechanism includes a radially expanding or axially expanding mechanism.

4. The medical device of claim 1, wherein at least of portion of the first extraluminal displacement mechanism is coiled between the two attachment points prior to activation of the extraluminal displacement mechanism.

5. The medical device of claim 4, wherein the coiled portion of the first extraluminal displacement mechanism uncoils after activation of the extraluminal displacement mechanism.

6. The medical device of claim 4, wherein at least one of the two attachment points is connected to the coiled portion of the first extraluminal displacement mechanism.

7. The medical device of claim 1, wherein at least one of the two attachment points is a collar not connected to the first extraluminal displacement mechanism.

8. The medical device of claim 1, wherein the medical device further comprises a third attachment point.

9. The medical device of claim 8, wherein the third attachment point is located along a mid-point of the first length.

10. The medical device of claim 1, wherein the self-activated shape memory polymer system comprises isobornyl acrylate, HEA, and HDDA in a weight ratio of 75:20:5.

11. The medical device of claim 1, wherein the self-activated shape memory polymer system comprises between 10 percent and 30 percent HEA.

12. The medical device of claim 1, wherein the self-activated shape memory polymer system comprises between 5 percent and 20 percent HDDA.

\* \* \* \* \*